US012746192B2

(12) United States Patent
Avery et al.

(10) Patent No.: US 12,746,192 B2
(45) Date of Patent: Sep. 29, 2026

(54) HAIR CONDITIONING COMPOSITION

(71) Applicant: Conopco, Inc., Englewood Cliffs, NJ (US)

(72) Inventors: Andrew Richard Avery, Wageningen (NL); Nerea Ortuoste Elcoro, Wageningen (NL)

(73) Assignee: Conopco, Inc., Englewood Cliffs, NJ (US)

( * ) Notice: Subject to any disclaimer, the term of this patent is extended or adjusted under 35 U.S.C. 154(b) by 261 days.

(21) Appl. No.: 18/704,017

(22) PCT Filed: Oct. 24, 2022

(86) PCT No.: PCT/EP2022/079586
§ 371 (c)(1),
(2) Date: Apr. 23, 2024

(87) PCT Pub. No.: WO2023/072828
PCT Pub. Date: May 4, 2023

(65) Prior Publication Data

US 2026/0151322 A1 Jun. 4, 2026

(30) Foreign Application Priority Data

Oct. 27, 2021 (EP) .................................... 21205126

(51) Int. Cl.

| | |
|---|---|
| *A61K 8/73* | (2006.01) |
| *A61K 8/04* | (2006.01) |
| *A61K 8/34* | (2006.01) |
| *A61K 8/41* | (2006.01) |
| *A61K 8/81* | (2006.01) |
| *A61Q 5/12* | (2006.01) |

(52) U.S. Cl.
CPC .............. *A61K 8/732* (2013.01); *A61K 8/042* (2013.01); *A61K 8/342* (2013.01); *A61K 8/416* (2013.01); *A61K 8/8111* (2013.01); *A61Q 5/12* (2013.01); *A61K 2800/34* (2013.01)

(58) Field of Classification Search
CPC ............................ A61K 8/732; A61K 2800/34
USPC .......................................................... 424/401
See application file for complete search history.

(56) References Cited

U.S. PATENT DOCUMENTS

| | | | |
|---|---|---|---|
| 4,149,551 A | 4/1979 | Benjamin et al. | |
| 6,368,582 B1 * | 4/2002 | Mitsumatsu ........... | A61K 8/375 424/70.28 |
| 6,416,751 B1 | 7/2002 | Roulier et al. | |
| 7,303,744 B2 | 12/2007 | Wells et al. | |
| 2005/0069511 A1 | 3/2005 | Magnet et al. | |
| 2006/0182702 A1 | 8/2006 | Lazzeri et al. | |
| 2006/0280714 A1 | 12/2006 | Maningat et al. | |
| 2014/0000643 A1 | 1/2014 | Swaile et al. | |
| 2016/0038397 A1 | 2/2016 | Markland et al. | |
| 2020/0155436 A1 | 5/2020 | Hartung et al. | |
| 2020/0323752 A1 | 10/2020 | Harkness et al. | |
| 2020/0368135 A1 | 11/2020 | Sjöö et al. | |

FOREIGN PATENT DOCUMENTS

| | | |
|---|---|---|
| CN | 113274338 | 8/2021 |
| EP | 1927346 | 6/2008 |
| FR | 2976488 | 12/2012 |
| WO | WO2017172117 | 10/2017 |

OTHER PUBLICATIONS

Search Report and Written Opinion in PCT/EP2022/077657 mailed Feb. 14, 2023.
Agrana Starch: EO-free Vitamin Shampoo with SynCrystal Ivory +CORN P04 PH "B", URL: https://www.agrana.com/fileadmin/inha lte/agrana_group/AGRANA_Starke/Kosmetikformulierungen/Men_Care/AGRANA_-_EO-free_Vita min_Shampoo_with_SynCrystal_Ivory_and_CORN_P04_PH_B.pdf; Apr. 5, 2012; 1 page.
Search Report and Written Opinion in PCT/EP2022/079586 mailed Mar. 10, 2023.
Agrana Starch: "Agrana Starch Granula Starches for Emulsions and Anhydrous Creams", URL: https://www.ulprospector.com/document s/1399420.pdf?bs=17598&b=443320&st=20&r=eu&ind=personalcare; Mar. 1, 2016; pp. 1-7.
Agrana Starch: "Dry Shampoo Mousse with RICE P04 Natural", URL: https://www.agrana.Com/fieldadmin/inhalte/agrana_group/2017/im ages/Starch/Golder/ Kosmetik/Formulierungen/AGRANA_-_Dry_Shampoo_Mousse_with_RI~CE_NS.Pdf; Jun. 12, 2018; 1 page.
Robert Y. Lochhead; The Role of Polymers in Cosmetics: Recent Trends, DOI: 10.1021/bk-2007-0961.ch001; The Role of Polymers in Cosmetics: Recent Trends, DOI: 10.1021/bk-2007-0961.ch001, Publication Date:Apr. 12, 2007, Chapter 1, pp. 3-56, ACS Symposium Series vol. 961, ISBN13: 9780841239968eISBN: 9780841220799 ; Apr. 12, 2007; 3-56; 961; American Chemical Society.

* cited by examiner

*Primary Examiner* — Walter E Webb
(74) *Attorney, Agent, or Firm* — Byrne Poh LLP; Nina R. Horan

(57) ABSTRACT

Excellent dry conditioning benefits are provided by a hair conditioner composition comprising: A) 0.01 to 5 wt %, by weight of the total composition, of a blend comprising i) particles of boiling resistant starch, having a Dv(50) particle size of from 1 to 12 microns; and ii) a hydrophobic non-silicone oil; in a weight ratio of starch to oil of from 0.5:1 to 1:0.5; B) 0.01 to 5 wt % of an emulsified non-silicone oil; wherein A) and B) are dispersed within: C) a conditioning gel phase comprising a cationic surfactant and a fatty material; and wherein the conditioner is free from silicone.

13 Claims, No Drawings

HAIR CONDITIONING COMPOSITION

FIELD OF THE INVENTION

The invention lies in the field of hair conditioner compositions that deliver conditioning benefits to hair, without the inclusion of silicone.

BACKGROUND OF THE INVENTION

Consumers desire hair treatments, such as shampoos and conditioners, that provide conditioning benefits, for example smoothness, ease of comb and softness to their hair.

The most widely used conditioning agents used in hair treatments products are silicones. They are widely recognised for their lubricating properties and the characteristically soft smooth feel they help create. Conditioning is achieved by the silicone being deposited onto the hair resulting in the formation of a film. The silicone film gives excellent conditioning and has been attributed to a wide range of benefits, for example, softness, smoothness and ease of comb.

The effectiveness of silicone as a conditioning agent can be largely attributed to its high lubricity, which in turn, confers a low coefficient of friction to treated hair.

So effective are silicones at delivering such benefits, that they have been the conditioning agent of choice, by formulators in the field, for over half a century. However, demand from the modern consumer for hair treatment compositions that are free from silicone has arisen over recent years.

Conditioning benefits are desired and perceived by the consumer both during and after the wash process. Thus, conditioning is evaluated both when the hair is wet and when it is dry. As such, it is desirable that rinse-off haircare products such as conditioners provide multiple benefits at different stages of use. Wet conditioning and dry conditioning are different benefits and are typically delivered in different ways.

The impact of the gel phase component of a conditioning product is most apparent when wet or damp hair is evaluated, as well as during application and distribution through the hair. At the post drying stages, conditioning benefits are primarily provided by silicones.

In silicone-free conditioner formulations alternative approaches are required to provide such benefits. However, the lubrication properties of silicone are unmatched in the field and suitable alternatives have proved a difficult need to fulfil.

Starches have been used in hair conditioning compositions:

US2006/0182702 (L'Oreal)—uses a composition comprising, a cationic surfactant, a starch which is preferably modified, a non-silicone cationic polymer with a cationic charge density of greater than or equal to 5 meq/g, and a nonionic non-polymeric solid compound with a melting point of greater than or equal to 35 degrees C. and/or with a viscosity, at a temperature of 40 degrees C. and at a shear rate of 1 $s^{-1}$, of greater than or equal to 1 Pa·s, to provide an improved conditioning effect to hair, especially smoothing of the ends.

FR2976488 (L'Oreal)—discloses a cosmetic composition comprising a combination of pumice particles (i); one or more starches (ii); one or more solid fatty alcohols (iii); and one or more fatty esters (iv) to provide durable treatment of keratin fibers that are damaged on the surface. A use for smoothing hair is disclosed. Distarch phosphate of pregelatinized hydroxypropyl maize is exemplified.

US2005069511 (L'Oreal) discloses a cosmetic composition, comprising, at least one starch, at least one carboxylic ester, water and up to 20 wt % of fatty phase relative to the total weight of composition. The use of these compositions, based on a specific ester and a starch allegedly provides hair that is easy to disentangle and is smooth from root to tip, with an improvement in the hold of the style. A pregelatinized corn distarch phosphate or Potato fecula modified with 2-chloro-ethylamidodipropionic acid neutralized with sodium hydroxide are utilised in the examples on wet hair to provide wet hair that is not heavy and hair shaping is easy.

US2016038397—(Penford Corp) dislcoses a cosmetic composition comprising: water; an ingredient selected from detergents and non-detersive conditioning agents; a cationic starch characterized by: a) an amylopectin/amylose weight ratio of greater than or equal to 60/40; b) an apparent cationic molecular weight of greater than or equal to 12 million daltons; and c) a cationic degree of substitution of from 0.5 meq/g to 2.5 meq/g to provide improved conditioning properties to personal care compositions. The personal care formulations can be used with or without silicone. Shampoos comprising cationic substituted starches allegedly give conditioning benefits in the wet stage.

EP1927346 discloses aqueous compositions for keratin fibres comprising an oil and/or wax, a natural starch, an emulsifier and a film forming polymer.

Despite the prior art, there remains a need for hair treatment compositions which are free from silicone yet are equally effective at conditioning the hair.

We have now surprisingly found that dry conditioning at parity with that achieved with silicone, as evidenced by delivery of low coefficient of friction, can be delivered from a conditioner by the use of a particulate boiling resistant starch, blended with an oil.

Definition of the Invention

In a first aspect, the invention provides a hair conditioner composition comprising A) 0.01 to 5 wt % (by weight of the total composition) of a blend comprising
   i) particles of a boiling resistant starch, having a Dv(50) particle size of from 1 to 12 microns; and
   ii) a hydrophobic non-silicone oil;
   in a weight ratio of starch to oil of from 0.5:1 to 1:0.5;
B) 0.01 to 5 wt % of an emulsified non-silicone oil;
   wherein A) and B) are dispersed within:
C) a conditioning gel phase comprising a cationic surfactant and a fatty alcohol; and wherein the conditioner is free from silicone.

In a second aspect, there is provided a method of treating hair, comprising the step of applying to hair a composition of the first aspect. Preferably, the method comprises the step of rinsing the composition from the hair. More preferably, the composition comprises the step of leaving the composition on the hair for from 20 seconds to 20 minutes, for example for 30 seconds to 10 minutes, and then rinsing from the hair.

Use is also provided, of a boiling resistant starch in a silicone free composition of the first aspect to provide conditioning benefits to hair. Use is also provided of a blend of boiling resistant starch particle and non-silicone oil in a silicone free composition of the first aspect to provide conditioning benefits to hair.

In the uses of the invention, the conditioning benefit is preferably a coefficient of friction that is equal to that conferred to hair treated with the same composition comprising silicone and that is free from boiling resistant starch.

DETAILED DESCRIPTION OF THE INVENTION

The hair conditioner composition of the invention comprises:

A) 0.01 to 5 wt % (by weight of the total composition) of a blend comprising:

i) a starch, which is a particulate boiling resistant starch, having a particle size of from 1 to 12 microns; and ii) a hydrophobic non-silicone oil; in a weight ratio of starch to oil of from 0.5:1 to 1:0.5.

The blend of starch and oil is present in an amount of from 0.01 to 5 wt %, preferably from 0.1 to 4 wt %, more preferably from 0.5 to 4 wt %, most preferably from 0.5 to 3 wt %.

The weight ratio of starch to oil in the blend, is from 0.5:1 to 1:0.5, preferably 1:1.

The Starch

The compositions of the invention comprise a starch, which is a particulate boiling resistant starch. Such starches are also known as "cook stable" or "Amylum Non Mucinaginosum" (ANM) starches. The starch remains particulate in the composition.

The starch for use in the invention has a Dv(50) particle size of from 1 to 12 microns, preferably from 2 to 10 microns, most preferably from 3 to 9 microns.

Any suitable particle size analyser, such as a Malvern Mastersizer 3000 may be used to characterize starch particles. A suitable refractive index (RI) of starch is 1.530 (as given in Holes in Starch Granules: Confocal, SEM and Light Microscopy Studies of Starch Granule Structure, Baldwin, P. M., Adler, J., Davies, M. C., Melia, C. D., Starch/Starke 46 (1994) Nr. 9, S. 341-346).

A laser diffraction technique may be employed. The sample is dispersed in water (which has a RI of 1.330) and passed into a sample window using a recirculating cell, where any particles present scatter the light. The refractive indices for both the particles and the suspending media are used for particle size determination. The following method may suitably be used:

Starch powder (0.1 g) is suspended in 10 mL of deionised water and pipetted into a Mastersizer 3000 Hydro Medium Volume cell until a 5% obscuration limit is reached. This process is preferably repeated three times for each starch sample at a stirrer speed of 2400 rpm. Results are reported here as 'particle size (μm) against volume (%)' for Dv(10), Dv(50) and Dv (90) indicating that 10%, 50% and 90% respectively, of particles are smaller than the quoted size The starches for use in the compositions of the invention are in the form of discrete particles.

The starches for use in the present invention remain in particulate form in the compositions of the invention.

The starch is not a gelatinised or "swelling" starch. Gelatinised, or gelatinisable starches do not remain as particles when incorporated in a formulation such as a hair treatment composition. Gelatinisation depends on the hydrophilic nature of the starch. In one study, Senanayake et al (International Journal of Food Science; Volume 2014, Article ID 148982; Suraji Senanayake, Anil Gunaratne, K. K. D. S. Ranaweera and Arthur Bamunuarachchi), starches substituted with hydroxypropyl groups showed significantly higher levels of swelling power and water-soluble index compared to the unmodified native starch. According to the authors, the presence of hydroxypropyl groups, which are hydrophilic, enhances the attraction of water molecules into the granular structure that causes early swelling in the granule.

A suitable type of boiling resistant starch is crosslinked. A preferred crosslinked boiling resistant starch is a di-starch phosphate. Most preferably, the boiling resistant starch is a crosslinked rice starch. Highly preferred boiling resistant rice starches may be selected from crosslinked di-phosphate starches (for example Rice PO4 Natural from Agrana Starch).

Preferably, the crosslinked boiling resistant starch is selected from crosslinked rice starch, crosslinked quinoa starch, crosslinked amaranth starch and mixtures thereof. More preferably, the starch is selected from crosslinked rice starch, crosslinked quinoa starch and mixtures thereof, most preferably the boiling resistant starch is crosslinked rice starch.

The starch is blended with a hydrophobic non-silicone oil. The starch particle is thus within a continuous oil phase.

The Hydrophobic Non-Silicone Oil (i)

The oils for use in the compositions of the invention are hydrophobic non-silicone oils.

Suitable hydrophobic non-silicone oils are selected from hydrocarbon oils, fatty ester oils and mixtures thereof.

The hydrocarbon oils can be natural or synthetic.

Straight chain hydrocarbon oils will preferably contain from about 12 to about 30 carbon atoms. Also suitable are branched chain hydrocarbon oils, which preferably contain from about 12 to about 42 carbon atoms. Also suitable are polymeric hydrocarbons of alkenyl monomers, such as C2 to C6 alkenyl monomers.

Specific examples of suitable hydrocarbon oils include paraffin oil, mineral oil, polyalphaolefin, squalane, saturated and unsaturated dodecane, saturated and unsaturated tridecane, saturated and unsaturated tetradecane, saturated and unsaturated pentadecane, saturated and unsaturated hexadecane, and mixtures thereof. Branched-chain isomers of these compounds, as well as of higher chain length hydrocarbons, can also be used. Another suitable material is polyisobutylene.

A preferred polyalphaolefin is commercially available as Silkflo 366™ (dec-1-ene) ex Ineos.

Suitable fatty esters are characterised by having at least 6 carbon atoms and include esters with hydrocarbyl chains derived from fatty acids or alcohols. Monocarboxylic acid esters include esters of alcohols and/or acids of the formula R'COOR in which R' and R independently denote alkyl or alkenyl radicals and the sum of carbon atoms in R' and R is at least 10, preferably at least 20. Di- and trialkyl and alkenyl esters of carboxylic acids can also be used.

Particularly preferred fatty esters are mono-, di- and triglycerides, more specifically the mono-, di-, and tri-esters of glycerol and long chain carboxylic acids such as C1-C22 carboxylic acids. Preferred materials include cocoa butter, palm stearin, sunflower oil, soyabean oil and coconut oil.

The hydrophobic non-silicone oil is preferably selected from hydrocarbon oils selected from paraffin oil, mineral oil, polyalphaolefin oil, esters with hydrocarbyl chains derived from fatty acids or alcohols and mixtures thereof.

Preferably, the oil is not a wax, particularly petrolatum and ozokerite.

The Emulsified Non-Silicone Oil

The compositions of the invention comprise an emulsified non-silicone oil. The oil is preferably described as above, for the hydrophobic non-silicone oil for use in the blend with the starch. The oil for use in the blend with the starch and the emulsified oil can be the same or different.

The emulsified non-silicone may be made by any suitable process and a skilled person in the art will know how to prepare such emulsified oils. In a preferred process the emulsified non-silicone oil may be produced via a catastrophic inversion process using a high shear homogeniser (for example, an Ultra Turrax T25 Basic S2 with a S25N-10G dispersing tool, from IKA, Germany). The emulsion may be formed by dropwise addition of water to a mixture of oil and surfactant under shear at a rate of, for example, 0.5 ml per minute prior to the inversion point.

The emulsifying surfactant(s) may be nonionic, cationic, or a mixture of nonionic and cationic and the inclusion level of the total surfactant amount may typically range from 0.1% to 2% by weight of the emulsion. Suitable nonionic surfactants will be known to those skilled in the art and may include for example Lutensol XP-79 (ex BASF). Suitable cationic surfactants will be known to a person skilled in the art and may include for example cetrimmonium chloride.

Silicone Free

The compositions of the invention are free from silicone. In the context of the invention, by free from is meant having less than 0.4 weight %, more preferably less than 0.1 weight %, even more preferably less than 0.05 weight %, still more preferably less than 0.001 weight %, yet preferably less than 0.0001 weight %, and most preferably 0 weight % of silicone by weight of the total composition.

Preferably, the compositions of the invention are also free from silanes.

The Conditioning Gel Base

The conditioning base comprises a cationic conditioning surfactant and a fatty alcohol.

The composition according to the invention comprises one or more conditioning surfactants which are cosmetically acceptable and suitable for topical application to the hair.

Suitable conditioning surfactants are selected from cationic surfactants, used singly or in admixture. Examples include quaternary ammonium cationic surfactants corresponding to the following general formula:

$$[N(R^1)(R^2)(R^3)(R^4)]^+ \quad (X)^-$$

in which $R^1$, $R^2$, $R^3$, and $R^4$ are each independently selected from (a) an aliphatic group of from 16 to 22 carbon atoms, or (b) an aromatic, alkoxy, polyoxyalkylene, alkylamido, hydroxyalkyl, aryl or alkylaryl group having up to 22 carbon atoms; and X is a salt-forming anion such as those selected from halide, (e.g. chloride, bromide), acetate, citrate, lactate, glycolate, phosphate nitrate, sulphate, and alkylsulphate, for example methosulphate, radicals. The aliphatic groups can contain, in addition to carbon and hydrogen atoms, ether linkages, and other groups such as amino groups. The aliphatic groups, e.g., those of about 12 carbons, or higher, can be saturated or unsaturated.

Specific examples of such quaternary ammonium cationic surfactants of the above general formula are cetyltrimethylammonium chloride, behenyltrimethylammonium chloride (BTAC), cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, cocotrimethylammonium chloride, dipalmitoylethyldimethylammonium chloride, PEG-2 oleylammonium chloride and salts of these, where the chloride is replaced by other halide (e.g., bromide), acetate, citrate, lactate, glycolate, phosphate nitrate, sulphate, or alkylsulphate.

In a preferred class of cationic surfactant of the above general formula, $R^1$ is a $C_{16}$ to $C_{22}$ saturated or unsaturated, preferably saturated, alkyl chain and $R^2$, $R^3$ and $R^4$ are each independently selected from $CH_3$ and $CH_2CH_2OH$, preferably $CH_3$.

Specific examples of such preferred quaternary ammonium cationic surfactants are cetyltrimethylammonium chloride (CTAC), behenyltrimethylammonium chloride (BTAC) and mixtures thereof.

Preferably, the quaternary ammonium cationic surfactant has a cation selected from cetyltrimethylammonium and behenyltrimethylammonium.

Alternatively, primary, secondary or tertiary fatty amines may be used in combination with an acid to provide a cationic surfactant suitable for use in the invention. The acid protonates the amine and forms an amine salt in situ in the hair care composition. The amine is therefore effectively a non-permanent quaternary ammonium or pseudo-quaternary ammonium cationic surfactant.

Suitable fatty amines of this type include amidoamines of the following general formula:

$$R^1—C(O)—N(H)—R^2—N(R^3)(R^4)$$

in which $R^1$ is a fatty acid chain containing from 12 to 22 carbon atoms, $R^2$ is an alkylene group containing from one to four carbon atoms, and $R^3$ and $R^4$ are each independently, an alkyl group having from one to four carbon atoms.

Specific examples of suitable materials of the above general formula are stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylamine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, and diethylaminoethylstearamide.

Also useful are dimethylstearamine, dimethylsoyamine, oyamine, myristylamine, tridecylamine, ethylstearylamine, N-tallowpropane diamine, ethoxylated (with 5 moles of ethylene oxide) stearylamine, dihydroxyethylstearylamine, and arachidyl behenylamine.

Particularly preferred is stearamidopropyldimethylamine.

The conditioning surfactant is present in the composition in a concentration of 0.1 to 10%, preferably at least 0.5%, more preferably at least 1%, still more preferably at least 2%, even more preferably at least 3% or even at least 4% but typically not more than 9%, preferably not more than 8%, more preferably not more than 7%, still more preferably not more than 6%, even more preferably not more than 5% by weight of the composition.

The Fatty Alcohol

The compositions of the invention comprise a fatty alcohol having a carbon-carbon chain length of from $C_8$ to $C_{22}$.

The combined use of fatty alcohols and cationic surfactants in conditioning compositions is preferred because this leads to the formation of a lamellar phase, in which the cationic surfactant is dispersed.

The fatty alcohol comprises from 8 to 22 carbon atoms, preferably 16 to 22, most preferably C16 to C18. Fatty alcohols are typically compounds containing straight chain alkyl groups. Preferably, the alkyl groups are saturated. Examples of preferred fatty alcohols include cetyl alcohol, stearyl alcohol and mixtures thereof. The use of these materials is also advantageous in that they contribute to the overall conditioning properties of compositions for use in the invention.

The level of fatty alcohol in conditioners for use in the invention will generally range from 0.01 to 10%, preferably from 0.1 to 8%, more preferably from 0.2 to 7%, most preferably from 0.3 to 6% by weight of the composition.

The weight ratio of cationic-surfactant to fatty alcohol is suitably from 1:1 to 1:10, preferably from 1:1.5 to 1:8, optimally from 1:2 to 1:5. If the weight ratio of cationic surfactant to fatty alcohol is too high, this can lead to eye irritancy from the composition. If it is too low, it can make the hair feel squeaky for some consumers.

A preferred conditioner comprises a conditioning gel phase having little or no vesicle content. Such conditioners and methods for making them are described in WO2014/016354, WO2014/016353, WO2012/016352 and WO2014/016351.

Such a conditioning gel phase comprises, by total weight of the composition, i) from 0.4 to 8 wt % of fatty alcohol having from 8 to 22 carbons, ii) from 0.1 to 2 wt % of cationic surfactant, and the composition confers a Draw Mass of from 1 to 250 g, preferably 2 to 100 g, more preferably 2 to 50 g, even more preferably 5 to 40 g and most preferably 5 to 25 g to hair treated with the composition.

Draw Mass is the mass required to draw a hair switch through a comb or brush. Thus the more tangled the hair the greater the mass required to pull the switch through the comb or brush, and the greater the level of condition of the hair, the lower the Draw Mass.

The Draw Mass is the mass required to draw a hair switch, for example of weight 1 to 20 g, length 10 to 30 cm, and width 0.5 to 5 cm through a comb or brush, as measured by first placing the hair switch onto the comb or brush, such that from 5 to 20 cm of hair is left hanging at the glued end of the switch, and then adding weights to the hanging end until the switch falls through the comb or brush.

Preferably, the hair switch is of weight 1 to 20 g, more preferably 2 to 15 g, most preferably from 5 to 10 g. Preferably, the hair switch has a length of from 10 to 40 cm, more preferably from 10 to 30 cm, and a width of from 0.5 to 5 cm, more preferably from 1.5 to 4 cm.

Most preferably, the Draw Mass is the mass required to draw a hair switch, for example of weight 10 g, length 20 cm, and width 3 cm through a comb or brush, as measured by first placing the hair switch onto the comb or brush, such that from 20 cm of hair is left hanging at the glued end of the switch, and then adding weights to the hanging end until the switch falls through the comb or brush.

Unless otherwise indicated, ratios, percentages, parts, and the like, referred to herein, are by weight.

Aspects of the invention will now be illustrated by the following examples.

EXAMPLES

Example 1: Preparation of Compositions for Use in the Ensuing Examples

Preparation of Composition 1 in Accordance with the Invention and Comparative Composition A The following conditioner compositions were prepared:

Compositions 1: Conditioner comprising a blend of oil with a boiling resistant particulate starch in accordance with the invention Composition A: Comparative conditioner comprising a blend of oil with a non-boiling-resistant particulate starch In the following table, the oil and starch are present in a blend.

The particle size of the particulate starches were measured using the method described herein.

TABLE 1

Composition of hair conditioner 1, in accordance with the invention and comparative conditioner A.

| | | Wt % in composition | |
|---|---|---|---|
| Ingredients | Tradename | A | 1 |
| Cetearyl alcohol | Ginol ™ 1618 TA | 3.2 | 3.2 |
| Behenyl trimethyl ammonium chloride | Genamin ™ BTLF (70% active) | 2.29 | 2.29 |
| Emulsified oil | Silkflo ™ 366/ Lutensol XP-79 (50% active) | 2 | 2 |
| Oil | Silkflo 366 | 1 | 1 |
| Starch (particle) | Rice PO4 Natural | — | 1.8 |
| Starch (particle) | D.S.A.7 | 1.8 | — |
| Chelating agent | EDTA | 0.05 | 0.05 |
| Salt | Sodium Chloride | 0.1 | 0.1 |
| Fragrance | — | 0.5 | 0.5 |
| Preservative | — | 0.06 | 0.06 |
| Water | — | up to 100 | up to 100 |

Rice PO4 Natural (boiling resistant starch) ex Agrana Starch, having a Dv(50) particle size of 7.66 micrometers D.S.A.7 starch (non-boiling resistant) ex Agrana Starch, having a Dv(50) particle size of 8.39 micrometers Silkflo 366: polyalphaolefin oil (dec-1-ene) ex Ineos Ginol 1618 TA ex Godrej Genamin BTLF ex Clariant The emulsified oil was produced via a catastrophic inversion process using an Ultra Turrax T25 Basic S2 high shear homogeniser and dispersing tool. Water was added dropwise to a mixture of oil and surfactant under shear in a 100 ml stainless steel beaker, at a rate of 0.5 ml per minute, prior to the inversion point. The resulting composition is given in Table 2.

TABLE 2 composition of the emulsified oil

| Ingredients | Tradename | Wt % in composition, by total weight of emulsified oil |
|---|---|---|
| Oil | Silkflo 366 | 50 |
| Emulsifier | Lutensol XP-79 | 0.5 |
| Water | Water | up to 100 |

The compositions in Table 1 were prepared as follows:

1. Water was added to a suitable vessel and heated to 80° C.
2. Surfactant and fatty materials were added to a suitable vessel and heated to above the melting point of the fatty materials to form a melt.

3. The melt was combined with the water phase and the resultant mixture mixed until opaque and thick.
4. The heat was then turned off and quench water was added.
5. The mixture was then cooled to below 40° C. and the rest of the materials, including the emulsified oil, fragrance, were added.
6. The starch and oil were mixed together to form a blend before being added to the composition.
7. Finally, the formulation was mixed at high shear on a Silverson mixer at 5000 rpm for 5 minutes.

Preparation of Examples 2 & 3 in Accordance with the Invention and Comparative Examples B & C Further compositions were prepared, using a different conditioner gel base, for use in the ensuing examples:

Compositions 2 & 3: Silicone free conditioner comprising a blend of oil with a boiling resistant particulate starch in accordance with the invention Compositions B & C: Comparative conditioners comprising a silicone but no starch/oil blend The emulsified oil and oil/starch blend were prepared as detailed above.

In the following table, the oil and starch are present in a blend.

TABLE 3

Composition of hair conditioner 2 & 3, in accordance with the invention and comparative conditioners B & C.

| | | Wt % in composition | | | |
|---|---|---|---|---|---|
| Ingredients | Tradename | B | C | 2 | 3 |
| Cetearyl alcohol | Ginol ™ 1618 TA | 4 | 3.2 | 4 | 3.2 |
| Behenyl trimethyl ammonium chloride | Genamin ™ BTLF (70% active) | 1 | 2.29 | 1 | 2.29 |
| Cationic surfactant | Lexamine ™ S-13 | 1 | — | 1 | — |
| Acid | Lactic acid | 0.32 | — | 0.32 | — |
| Emulsified oil | Silkflo ™ 366/ Lutensol XP-79 (50% active) | 2 | 2 | 2 | 2 |
| Oil | Silkflo 366 | — | — | 1 | 1 |
| Starch (particle) | Rice PO4 Natural | — | — | 1 | 1 |
| Silicone | Xiameter MEM-7134 (70% active) | 2.85 | 2.85 | — | — |
| Chelating agent | EDTA | 0.05 | 0.05 | 0.05 | 0.05 |
| Salt | Sodium Chloride | 0.1 | — | 0.1 | — |
| Fragrance | — | 0.5 | 0.5 | 0.5 | 0.5 |
| Preservative | — | 0.06 | 0.06 | 0.06 | 0.06 |
| Water | — | up to 100 | up to 100 | up to 100 | up to 100 |

Rice PO4 Natural ex Agrana Starch, having a Dv(50) particle size of 7.66 micrometers Silkflo 366: polyalphaolefin oil (dec-1-ene) ex Ineos Ginol 1618 TA ex Godrej Genamin BTLF ex Clariant The compositions in Table 3 were prepared as follows:

1. Water was added to a suitable vessel, any lactic acid was added and the vessel heated to 80° C.
2. Surfactants and fatty materials were added to a suitable vessel and heated to above the melting point of the fatty materials to form a melt.
3. The melt was combined with the water phase and the resultant mixture mixed until opaque and thick.
4. The heat was then turned off and quench water was added.
5. The mixture was then cooled to below 40° C. and the rest of the materials, including the emulsified oil, fragrance and silicone (if required) were added.
6. The starch and oil were mixed together to form a blend before being added to the composition.
7. Finally, the formulation was mixed at high shear on a Silverson mixer at 5000 rpm for 5 minutes.

Example 3: Effect of Compositions 1 and a on Coefficient of Friction of Treated Hair Compositions 1, according to the invention and comparative A were used to treat hair. The hair was treated using the following method:

5 g 10 inch Dark Brown European switches were wetted under a tap. A solution of 14 wt % sodium laureth sulfate with one unit of ethoxylation was applied to the switch (at 0.1 g per gram of hair). The switch was massaged for 30 seconds and then rinsed under the tap for 30 seconds. This was repeated. The wet switches were then detangled using a comb. The conditioner composition (0.2 g per gram hair) was then applied to the hair and massaged for 1 min, before being rinsed for 1 min under a controlled flow of water. The switches were left to dry at room temperature.

The coefficient of friction of the hair following treatment was then analysed using a device based upon a flat plate attached to multiple force transducers, with appropriate signal processing and data acquisition. Examples of suitable devices and are described in Guest S. et al, Journal of Cosmetics, Dermatological Sciences and Applications, Vol. 3, 2013, pp. 66-78 and Guest S. et al, Journal of Texture Studies, Vol. 43, 2012, pp. 77-93, and references therein. The specific device used herein employed a Micro Analog 3 signal processing system (Fylde Electronic Laboratories Ltd., UK), along with Dasylab data acquisition software (National Instruments, USA) and six 10 Newton capacity, SMT1 force transducers (Interface Inc., USA) attached to a glass-balsa panel (Aerospace Composite Products, USA). Data presented herein were collected by an operator running a finger along the surface of a dried, treated hair tress (described above), laid flat upon the device, to allow the recording of friction and load forces and calculation of the resulting friction coefficient.

The results are given in Table 4 below:

TABLE 4

Coefficient of friction of hair treated with Compositions 1 and Comparative composition A

| Composition | Coefficient of friction | 95% C.I* |
|---|---|---|
| Comparative A | 0.15 | 0.02 |
| Example 1 | 0.12 | 0.02 |

*95% confidence interval

The results show that with the composition according to the invention (Example 1), with a boiling resistant particulate starch, a lower coefficient of friction is obtained than for the comparative examples comprising a non-boiling resistant comparative starch.

Example 4: Effect of Compositions 2 & 3 and B & C on Coefficient of Friction of Treated Hair Compositions 2 & 3, according to the invention and comparatives B & C were used to treat hair.

The hair was treated using the method described above and coefficient of friction measured as above.

The results are given in Table 5 below:

TABLE 5

Coefficient of friction of hair treated with Compositions 2 & 3 and Comparative composition B & C

| | Coefficient of friction | 95% C.I* |
|---|---|---|
| Comparative B | 0.15 | 0.004 |
| Comparative C | 0.13 | 0.018 |
| Example 1 | 0.15 | 0.010 |
| Example 2 | 0.13 | 0.016 |

*95% confidence interval

The results show that the compositions according to the invention Example 1 and Example 2, non-silicone compositions confer a coefficient of friction to hair that is equal to the coefficient of friction of hair treated with the comparative compositions that contain silicone.

The invention claimed is:

1. A hair conditioner composition comprising

A) 0.01 to 5 wt %, by weight of the total composition, of a blend comprising i) particles of boiling resistant starch, having a Dv(50) particle size of from 1 to 12 microns; and ii) a hydrophobic non-silicone oil;

in a weight ratio of starch to oil of from 0.5:1 to 1:0.5;

B) 0.01 to 5 wt % of an emulsified non-silicone oil;

wherein A) and B) are dispersed within:

C) a conditioning gel phase comprising a cationic surfactant and a fatty material; and wherein the conditioner is free from silicone.

2. The composition of claim 1, wherein the boiling resistant starch is crosslinked.

3. The composition of claim 2, wherein the boiling resistant starch is selected from a crosslinked rice starch, a crosslinked quinoa starch, a crosslinked amaranth starch and mixtures thereof.

4. The composition of claim 1, wherein the boiling resistant starch is a crosslinked di-phosphate rice starch.

5. The composition of claim 1, wherein the boiling resistant starch has a Dv(50) particle size of from 3 to 9 microns.

6. The composition of claim 1, wherein the hydrophobic non-silicone oil is selected from hydrocarbon oils, fatty ester oil and mixtures thereof.

7. The composition of claim 6, wherein the hydrophobic non-silicone oil is selected from paraffin oil, mineral oil, polyalphaolefin, squalane, esters with hydrocarbyl chains derived from fatty acids or alcohols and mixtures thereof.

8. The composition of claim 1, wherein the emulsified non-silicone oil is selected from paraffin oil, mineral oil, polyalphaolefin, squalane, esters with hydrocarbyl chains derived from fatty acids or alcohols and mixtures thereof.

9. The composition of claim 1, wherein the cationic surfactant is a quaternary ammonium cationic surfactant.

10. The composition of claim 9, wherein the quaternary ammonium cationic surfactant has a cation selected from cetyltrimethylammonium and behenyltrimethylammonium.

11. The composition of claim 1, wherein the fatty material has a carbon-carbon chain length of C8 to C22.

12. A method of treating hair, comprising the step of applying a composition of claim 1, to hair.

13. The composition of claim 3, wherein the boiling resistant starch is crosslinked rice starch.

* * * * *